US010559385B2

(12) United States Patent
Sengupta et al.

(10) Patent No.: US 10,559,385 B2
(45) Date of Patent: Feb. 11, 2020

(54) FORECASTING A PATIENT VITAL MEASUREMENT FOR HEALTHCARE ANALYTICS

(71) Applicant: Conduent Business Services, LLC, Dallas, TX (US)

(72) Inventors: Abhishek Sengupta, West Bengal (IN); Bhupendra Singh Solanki, Madhya Pradesh (IN); Prathosh Aragulla Prasad, Karnataka (IN); Vaibhav Rajan, Bangalore (IN); Katerina Ocean Sinclair, Tucson, AZ (US); Stephen Fullerton, Jacksonville Beach, FL (US); Satya Narayan Shukla, Uttar Pradesh (IN)

(73) Assignee: CONDUENT BUSINESS SERVICES, LLC, Florham Park, NJ (US)

( * ) Notice: Subject to any disclaimer, the term of this patent is extended or adjusted under 35 U.S.C. 154(b) by 965 days.

(21) Appl. No.: 15/132,460

(22) Filed: Apr. 19, 2016

(65) Prior Publication Data

US 2017/0300646 A1 Oct. 19, 2017

(51) Int. Cl.
*G16H 50/20* (2018.01)
*G06N 7/00* (2006.01)
(Continued)

(52) U.S. Cl.
CPC ........... *G16H 50/20* (2018.01); *A61B 5/7275* (2013.01); *G06N 7/005* (2013.01); *G16H 50/50* (2018.01);
(Continued)

(58) Field of Classification Search
CPC ........... A61B 5/01; A61B 5/021; A61B 5/024; A61B 5/0816; A61B 5/14532; A61B 5/14542; G06N 7/005; G16H 50/20
See application file for complete search history.

(56) References Cited

U.S. PATENT DOCUMENTS

| 2006/0025931 A1* | 2/2006 | Rosen | G16H 50/20 702/19 |
| 2010/0280985 A1* | 11/2010 | Duchon | G06N 7/005 706/52 |

* cited by examiner

*Primary Examiner* — Taelor Kim
(74) *Attorney, Agent, or Firm* — Jones Robb, PLLC (57) ABSTRACT

What is disclosed is a system and method for forecasting and imputing an unknown vital measurement of a patient. Temporally successive patient vital measurements are received which comprise irregularly sampled observations $\{y_1, \ldots, y_N\}$, where $y_j$ denotes the $j^{th}$ observation at time $t_j$, and N is the number of samples. The vital measurements are then provided to a model trained using historical data of patient vital measurements. The model generates a parameter set $\theta=(A,B,C)$, where A is a state transition matrix, B is a control matrix, and C is a matrix which maps state-space variables to observation variables. The parameters are used to obtain state-space variable $z_t$ which, in turn, is used to forecast an unknown observation $y_{N+1}$ or to impute an unknown observation $y_t$, where $1<t<N$. The historical data is then updated with the forecasted observation $y_{N+1}$ or the imputed unknown observation $y_t$.

18 Claims, 4 Drawing Sheets

(51) Int. Cl.
  *A61B 5/00*    (2006.01)
  *A61B 5/021*   (2006.01)
  *A61B 5/024*   (2006.01)
  *A61B 5/01*    (2006.01)
  *A61B 5/08*    (2006.01)
  *G16H 50/50*   (2018.01)
  *A61B 5/145*   (2006.01)
(52) U.S. Cl.
  CPC .................. *A61B 5/01* (2013.01); *A61B 5/021* (2013.01); *A61B 5/024* (2013.01); *A61B 5/0816* (2013.01); *A61B 5/14532* (2013.01); *A61B 5/14542* (2013.01)

| METHOD | BASELINE | | OUR MODEL | |
|---|---|---|---|---|
| RMSE | BPS | BPD | BPS | BPD |
| TEST 1 | 0.64 | 0.71 | 0.40 | 0.43 |
| TEST 2 | 0.63 | 0.77 | 0.41 | 0.44 |
| TEST 3 | 0.65 | 0.68 | 0.40 | 0.44 |
| TEST 4 | 0.64 | 0.67 | 0.42 | 0.44 |
| TEST 5 | 0.61 | 0.67 | 0.40 | 0.44 |

(TABLE 1)

| R.M.S.E | BPS | HR | RR | TEMP |
|---|---|---|---|---|
| TEST 1 | 0.42 | 0.36 | 0.38 | 0.40 |
| TEST 2 | 0.44 | 0.38 | 0.38 | 0.39 |
| TEST 3 | 0.45 | 0.37 | 0.37 | 0.40 |
| TEST 4 | 0.43 | 0.38 | 0.37 | 0.40 |
| TEST 5 | 0.44 | 0.38 | 0.36 | 0.41 |

(TABLE 2)

| TEST CASE | MICE | | MTSDI | | AMELIA II | | OUR MODEL | |
|---|---|---|---|---|---|---|---|---|
| | BPS | BPD | BPS | BPD | BPS | BPD | BPS | BPD |
| 1 | 0.99 | 0.98 | 0.55 | 0.56 | 0.99 | 0.95 | 0.19 | 0.18 |
| 2 | 1.08 | 1.05 | 0.62 | 0.60 | 0.95 | 0.96 | 0.20 | 0.20 |
| 3 | 1.06 | 1.05 | 0.54 | 0.60 | 0.93 | 0.94 | 0.16 | 0.19 |
| 4 | 1.09 | 1.11 | 0.61 | 0.62 | 0.93 | 0.92 | 0.17 | 0.19 |
| 5 | 0.99 | 1.01 | 0.52 | 0.54 | 0.97 | 0.92 | 0.17 | 0.19 |

(TABLE 3)

FIG. 4

FORECASTING A PATIENT VITAL MEASUREMENT FOR HEALTHCARE ANALYTICS

TECHNICAL FIELD

The present invention is directed to systems and methods for forecasting and/or imputing an unknown vital measurement for patient healthcare analytics.

BACKGROUND

Vitals such as blood pressure, heart rate, respiration rate etc. are regularly monitored in hospitals to evaluate the physiological condition of a patient. The levels and trends in these signals can provide a wealth of information for disease progression, effects of drugs, the state of various organs, system problems, and the like. Such vitals are usually temporally successive measurements. Methods for accurately modeling patient physiological signals are increasingly needed to support clinical decisions and provide predictive tools.

To model physiological signals, one has to address the challenges of modeling the underlying dynamics of physiological systems that are not well modeled. Further, most predictive analytics tools use physiological signals to build their models. These measurements are typically not obtained at exact periodic intervals. At a given time-point, not all vitals of a patient may be measured, resulting in a number of missing values in the physiological data. Measurement data can be missing due to errors in recording, errors in the measurement devices, etc. Model-based methods which can forecast and impute missing patient vital measurement are increasingly needed for use in ICU Admission Prediction Systems which help identify patients requiring ICU admission, and in Emerging Complications Prediction Systems which help identify patients at risk for developing complications during their hospital stay. The present invention is specifically directed to forecasting and imputing patient vital measurements for healthcare analytics.

BRIEF SUMMARY

What is disclosed is a system and computer implemented method for forecasting and/or imputing an unknown vital measurement for patient healthcare analytics. The present method utilizes a statistical approach to learn the underlying system dynamics using multiple sequences of physiological data obtained from different patients while simultaneously addressing the challenge of irregular sampling. The model disclosed herein has been effective at modelling irregularly sampled physiological data to forecast future vitals and impute values for missing vitals. This model finds it's uses in diverse applications in the field of healthcare analytics. The forecasted and imputed vitals can provide timely alerts when vital signs are expected to deviate from an expected range thereby leading to effective triage and better intervention.

One embodiment of the present method involves the following. First, temporally successive patient vital measurements are received for processing. The vital measurements can be, for example, blood pressure, respiration rate, heart rate, body temperature, or a combination thereof. More particularly, the vital measurements comprise irregularly sampled observations $\{y_1, \ldots, y_N\}$, where $y_j$ denotes the $j^{th}$ observation at time $t_j$, and N is the number of samples. The received vital measurements are then provided to a model which has been trained using historical data of patient vital measurements. In a manner more fully disclosed herein, the model is trained using historical data of patient vital measurements. The model generates a parameter set $\theta=(A,B,C,Q,R)$, where A is a state transition matrix, B is a control matrix, C is a matrix which maps state-space variables to observation variables, Q is an amount of noise in the state-space variables, and R is an amount of noise in the observation variables. The parameters generated are used to obtain state-space variable(s) $z_t$. Embodiments for $z_t$ are disclosed herein. The obtained state-space variables are used to forecast an unknown observation $y_{N+1}$. The historical data of patient vital measurements is then updated with the forecasted observation. In another embodiment, the state-space variables are used to impute an unknown observation $y_t$, where $1 < t < N$. The historical data of patient vital measurement is then updated with the imputed observation.

Features and advantages of the above-described method will become readily apparent from the following detailed description and accompanying drawings.

BRIEF DESCRIPTION OF THE DRAWINGS

The foregoing and other features and advantages of the subject matter disclosed herein will be made apparent from the following detailed description taken in conjunction with the accompanying drawings, in which.

DETAILED DESCRIPTION

What is disclosed is a system and computer implemented method for forecasting and/or imputing an unknown vital measurement for patient healthcare analytics.

Non-Limiting Definitions

A "patient" refers to a living being. Although the term "person", "patient" or "subject" may be used throughout this disclosure, the patient may be something other than a human such as, for example, a primate. Therefore, the use of such terms is not to be viewed as limiting the scope of the appended claims strictly to humans.

Figure 1:
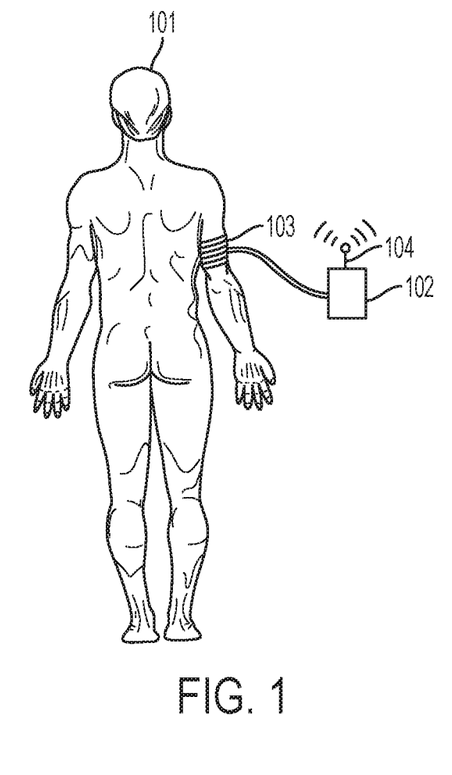
FIG. 1 illustrates an example vitals measuring device capturing temporally successive vital measurements using specialized sensors attached to the arm of a patient.

A "vital measurement" refers to any measurement associated with patient vital signs. Vital signs, or simply vitals, are used to measure the body's basic functions and help medical professionals assess the physical health of a person and gauge progress toward recovery. FIG. 1 illustrates an example vitals measuring device 102 capturing temporally successive vital measurements using specialized sensors 103 attached to the arm of a patient 101. Antenna 104 provides an example means by which the captured vital measurements are wirelessly communicated to a remote computing device (not shown) for processing in accordance with the teachings hereof. The normal ranges for a person's vital signs vary with age, weight, gender, and overall health. There are four primary vital signs: body temperature, blood pressure, heart rate, and respiratory rate, often notated as BT, BP, HR, and RR. Depending on the clinical setting, the vital signs may include other measurements such as blood glucose, oxygen saturation, blood $CO_2$, and Glasgow Coma Scale. These measurements are most often not recorded at regular intervals. Typically vitals are recorded every 3-4 hours as needed, and this interval may vary widely depending on hospital protocols and severity of the patient. In critical care, measurements may be made at intervals ranging from a second to a minute. One skilled in the medical arts would be readily familiar with various medical devices and operative steps used by trained personnel to obtain vital measurements from a patient. As such, a discussion as to devices and methods for obtaining a particular patient vital is omitted herein. Patient vitals and other patient data are typically stored in the form of Electronic Medical Records.

"Receiving vital measurements" is intended to be widely construed and includes retrieving, obtaining, capturing, calculating or otherwise acquiring patient vitals for processing in accordance with the methods disclosed herein. The patient vitals can be retrieved from Electronic Medical Records. Vital measurements can be obtained from a memory, storage device, or from a media such as a CDROM, DVD, and the like. Vital measurements can be obtained from a remote device over a network or downloaded from a web-based system or application which makes such measurements available. The received vital measurements are provided to a model.

A "model", as taught herein, receives an input and generates an output. The model hereof uses historical data of patient vital measurements and generates a parameter set $\theta=(A,B,C,Q,R)$, where A is a state transition matrix, B is a control matrix, C is a matrix which maps state-space variables to observation variables, Q is an amount of noise in the state-space variables, and R is an amount of noise in the observation variables. The present model is based on a Kalman Filter which adopts a statistical approach to learn the underlying system dynamics.

A "Kalman Filter" was developed by Rudolph Emil Kalman and disclosed in "A New Approach To Linear Filtering And Prediction Problems", Journal of Fluids Engineering, 82(1):35-45, (1960). The Kalman Filter has been extensively used in many fields involving time series analysis and modeling: navigation and control of vehicles/robots, image, video and speech processing, among many others. It is a linear dynamical system that models a sequence of measurements and an underlying sequence of states that represents the system dynamics, with the assumption that both the state-evolution and measurement sequences are corrupted by noise. Such models attempt to capture the dynamics of the system states that govern that temporal evolution of the measurements unlike static models such as support vector machines and random forests wherein the temporal dependencies between successive measurements in time are usually not modeled. In its usual embodiment, a Kalman Filter has a deterministic iterative closed-form solution given the knowledge of the dynamics of the system and parameters of the noise involved. In most scenarios, system dynamics are known from the laws of the physical system being modeled.

The Present Model

The present model is formulated as follows:

$$z_t = Az_{t-1} + B\Delta_{t,t-1} + \in_t \quad (1)$$

$$y_t = Cz_t + \delta_t \quad (2)$$

where $z_t \in \mathbb{R}^k$ and $y_t \in \mathbb{R}^p$ denotes the hidden or state-space variables and observation variables, respectively, at time t, $A_{k \times k}$ denotes the underlying state transition matrix, B is a control matrix, $\Delta_{t,t-1}$ denotes a time difference between the $t^{th}$ and the $(t-1)^{th}$ observation, $C_{p \times k}$ denotes the observation matrix which maps the state-space variables $z_t$ into the observed variables $y_t$, and $\in_t$ and $\delta_t$ are the noise corrupting the state-space and observation variables, respectively. We assume that both the process noise and the observation noise are zero-mean Gaussian with an unknown co-variance, i.e., $\in_t \sim \mathcal{N}(0, Q), \delta_t \sim \mathcal{N}(0, R)$. For the problem at hand, the noise statistics as well as the system dynamics are unknown. Thus, we include both noise statistics and system dynamics in our parameter set $\theta=(A,B,C,Q,R)$ and attempt to learn them through a maximum likelihood approach using the data, taking into account the irregular sampling through the term $B\Delta_{t,t-1}$. All parameters in the set $\theta$ can be estimated using Expectation Maximization (EM) given N sequential observations $y_i = \{y_{i1}, \ldots, y_{iT_i}\}$, $i = 1 \ldots N$, each of different lengths $T_i$. The general EM framework is as follows.

General EM Framework

Given data Y, unobserved latent variables Z, and unknown parameter set $\theta$, we obtain the maximum-likelihood estimate of $\theta$ where the likelihood is given by:

$$L(\theta; X) = p(X|\theta) = \sum_Z p(X, Z|\theta). \quad (3)$$

In many cases, including the present case, this quantity is intractable and so EM is used to iteratively estimate the parameters using the following two steps with suitable initial values $\theta^{(0)}$ and a predetermined termination criterion.

Two steps are used to obtain $p(z_t|y_t) \sim \mathcal{N}(\mu_t, \Sigma_t)$:

Prediction Step:

$$p(Z_t|y_{1:t-1}) \sim \mathcal{N}(\mu_{t|t-1}, \Sigma_{t|t-1}) \quad (4)$$

where:

$$\mu_{t|t-1} = A\mu_{t-1} + B\Delta_{t,t-1} \quad (5)$$

$$\Sigma_{t|t-1} = A\Sigma_{t-1}A' + Q \quad (6)$$

Measurement Step:

$$\Sigma_t = (I - K_t C)\Sigma_{t|t-1} \quad (7)$$

where the Kalman Gain is given by:

$$K_t = \Sigma_{t|t-1} C' S_t^{-1} \quad (8)$$

$$S_t = Cov(r_t|y_{1:t-1}) \quad (9)$$

$$r_t = y_t - \hat{y}_t; \hat{y}_t = E(y_t|y_{1:t-1}) \quad (10)$$

$$\mu_t = \mu_{t|t-1} + K_t r_t \quad (11)$$

Kalman Smoothing

To obtain $p(z_t|y_{1:T}) \sim \mathcal{N}(\mu_{t|T}, \Sigma_{t|T})$:

$$\mu_{t|T} = \mu_t + J_t(\mu_{t+1|T} - \mu_{t+1|t}) \quad (12)$$

$$\Sigma_{t|T} = \Sigma_t + J_t(\Sigma_{t+1|T})J_t' \quad (13)$$

$$J_t = \Sigma_t A' \Sigma_{t+1|t}^{-1} \quad (14)$$

where $\mu_T$ and $\Sigma_t$ are as follows.

$$\frac{\partial l(\theta|D)}{\partial \mu_1} = \Sigma_1^{-1} \sum_{i=1}^{N}(\widehat{z_{t1}} - \mu_1) = 0 \Rightarrow \mu_1^{(1)} = \frac{1}{N} \sum_{i=1}^{N} \widehat{z_{t1}} \quad (15)$$

-continued $$\frac{\partial l(\theta|D)}{\partial \Sigma_1^{-1}} = \tag{16}$$

$$\frac{1}{2}N\Sigma_1 - \frac{1}{2}\left(\sum_{i=1}^N (\bar{z}_{t1}z_{t1}^T) - \sum_{i=1}^N \widehat{z_{t1}}\mu_1^{(1)'} - \mu_1^{(1)}\sum_{i=1}^N \widehat{z_{t1}}' + \mu_1^{(1)}\mu_1^{(1)'}\right) \Rightarrow$$

$$\Sigma_1^{-1} = \frac{1}{N}\sum_{i=1}^N (\bar{z}_{t1}z_{t1}^T) +$$

$$\frac{1}{N}\left\{\sum_{i=1}^N (\widehat{z_{t1}} - \bar{\hat{z}}_1)(\widehat{z_{t1}} - \bar{\hat{z}}_1)'\right\} - \frac{1}{N}\sum_{i=1}^N \widehat{z_{t1}}\widehat{z_{t1}}'$$

where:

$$\bar{\hat{z}}_1 = \frac{1}{N}\sum_{i=1}^N \widehat{z_{t1}} \tag{17}$$

Calculate the expected value of the likelihood function with respect to the conditional distribution of Z|X with the current estimates $\theta^{(t)}$:

$$\theta^{(t)}: Q(\theta|\theta^{(t)}) = E_{Z|X,\theta^{(t)}}[\log L(\theta; X, z)]. \tag{18}$$

$$\hat{z}_t = W(z_t|y_{1:T}) = \mu_{t|T} \tag{19}$$

$$\widehat{z_t z_t'} = E(z_t z_t'|y_{1:T}) = \Sigma_{t|T} + \mu_{t|T}\mu_{t|T}' \tag{20}$$

$$(\widehat{z_t z_{t-1}'}) = E(z_t z_{t-1}'|y_{1:T}) = Cov(z_t, z_{t-1}|y_{1:T}) + \mu_{t|T}\mu_{t-1}' \tag{21}$$

$$Cov(z_t, z_{t-1}|y_{1:T}) \stackrel{\Delta}{=} \tag{22}$$

$$\Sigma_{t,t-1|T} = \Sigma_{t|t}J_{t-1}' + J_t(\Sigma_{t+1,t|T} - A\Sigma_{t|t})J_{t-1}'$$

where:

$$\Sigma_{T,T-1|T} = (I - K_T C)A\Sigma_{T-1|T-1} \tag{23}$$

Find current parameter estimates that maximizes:

$$\theta^{(t+1)} = \operatorname{argmax}_\theta Q(\theta|\theta^{(t)}) \tag{24}$$

Assuming the hidden states to be known, the likelihood of the data (for a signal observation sequence) is given by:

$$L(\theta|D) = p(z_1)\prod_{t=2}^T p(z_t|z_{t-1})\prod_{t=1}^T p(y_t|z_t) \tag{25}$$

where $p(z_1) \sim \mathcal{N}(\mu_1, \Sigma_1)$;
$p(z_t) \sim \mathcal{N}(A_{z_{t-1}} + B\Delta_{t,t-1}, Q)$, and $p(y_t|z_t) \sim \mathcal{N}(C_{z_t}, R)$.

The log likelihood of the data is given by:

$$l(\theta|D) = -\frac{1}{2}\log|\Sigma_1| - \frac{1}{2}(z_1 - \mu_1)'\Sigma_1^{-1}(z_1 - \mu_1) - \tag{26}$$

$$\sum_{t=2}^T \left\{\frac{1}{2}(z_t - A_{z_{t-1}} - B\Delta_{t,t-1})'Q^{-1}(z_t - A_{z_{t-1}} - B\Delta_{t,t-1})\right\} -$$

$$\frac{1}{2}(T-1)\log|Q| - \sum_{t=1}^T \left\{\frac{1}{2}(y_t - C_{z_t})'R^{-1}(y_t - C_{z_t})\right\} -$$

$$\frac{1}{2}T\log|R| - \frac{1}{2}T(p+k)\log 2\pi.$$

For N observation sequences, a modified log likelihood is given by:

$$l(\theta|D) = -\frac{1}{2}N\log|\Sigma_1| - \frac{1}{2}(z_{i1} - \mu_1)'\Sigma_1^{-1}(z_{i1} - \mu_1) - \tag{27}$$

$$\sum_{i=1}^N \sum_{t=2}^{T_i} \left\{\frac{1}{2}(z_{it} - A_{z_{i(t-1)}} - B\Delta_{i,t,t-1})'Q^{-1}(z_{it} - A_{z_{i(t-1)}} - B\Delta_{i,t,t-1})\right\} - \frac{1}{2}\sum_{i=1}^N (T_i - 1)\log$$

$$|Q| - \sum_{i=1}^N \sum_{t=1}^T \left\{\frac{1}{2}(y_{it} - C_{z_{it}})'R^{-1}(y_{it} - C_{z_{it}})\right\} - \frac{1}{2}\sum_{i=1}^N T_i\log|R| - \frac{1}{2}\sum_{i=1}^N T_i(p+k)\log 2\pi.$$

Derivation of parameter set $\theta$

Parameter A:

$$\frac{\partial l(\theta|D)}{\partial A} = -\sum_{i=1}^N \sum_{t=2}^{T_i} Q^{-1}(\widehat{z_{it}z_{i(t-1)}'}) + \tag{28}$$

$$\sum_{i=1}^N \sum_{t=2}^{T_i} Q^{-1}A(\widehat{z_{i(t-1)}z_{i(t-1)}'}) + \sum_{i=1}^N \sum_{t=2}^{T_i} Q^{-1}B\Delta_{t,t-1}\widehat{z_{i(t-1)}'} = 0$$

$$A^{(1)} = \left(\sum_{i=1}^N \sum_{t=2}^{T_i} (\widehat{z_{it}z_{i(t-1)}'}) - \sum_{i=1}^N \sum_{t=2}^{T_i} B\Delta_{i,t,t-1}\widehat{z_{i(t-1)}'}\right) \tag{29}$$

$$\left(\sum_{i=1}^N \sum_{t=2}^{T_i} (\widehat{z_{i(t-1)}z_{i(t-1)}'})\right)^{-1}$$

where:

$$(\widehat{z_{it}z_{i(t-1)}'}) = E(z_{it}z_{i(t-1)}'|y_{1:T_i}) \tag{30}$$

Parameter B:

$$\frac{\partial l(\theta|D)}{\partial B} = -\sum_{i=1}^N \sum_{t=2}^{T_i} Q^{-1}\widehat{z_{it}}\Delta_{i,t,t-1}' + \tag{31}$$

$$\sum_{i=1}^N \sum_{t=2}^{T_i} Q^{-1}A\widehat{z_{i(t-1)}}\Delta_{i,t,t-1}' + \sum_{i=1}^N \sum_{t=2}^{T_i} Q^{-1}B\Delta_{i,t,t-1}\Delta_{i,t,t-1}' =$$

-continued $$0 \Rightarrow B^{(1)} = \left(\sum_{i=1}^{N}\sum_{t=2}^{T_i} \widehat{z_{it}}\Delta'_{i,t,t-1} - \sum_{i=1}^{N}\sum_{t=2}^{T_i} A\widehat{z_{i(t-1)}}\Delta'_{i,t,t-1}\right)$$
$$\left(\sum_{i=1}^{N}\sum_{t=2}^{T_i} \Delta_{i,t,t-1}\Delta'_{i,t,t-1}\right)^{-1}$$

Parameter C:

$$\frac{\partial l(\theta|D)}{\partial C} = -\sum_{i=1}^{N}\sum_{t=1}^{T_i} R^{-1} y_{it}\widehat{z_{it}}' + \sum_{i=1}^{N}\sum_{t=1}^{T_i} R^{-1} C\widehat{z_{it}z_{it}^T} = \quad (32)$$

$$0 \Rightarrow C^{(1)} = \left(\sum_{i=1}^{N}\sum_{t=1}^{T_i} y_{it}\widehat{z_{it}}'\right)\left(\sum_{i=1}^{N}\sum_{t=1}^{T_i} (\widehat{z_{it}z_{it}^T})\right)^{-1}$$

where:

$$\widehat{z_{it}} = E(z_{it}|y_{1:T_i}); \quad (\widehat{z_{it}z_{it}^T}) = E(z_{it}z'_{it}|y_{1:T_i}) \quad (33)$$

Parameter Q:

$$Q^{(1)} = \frac{1}{\sum_{i=1}^{N}(T_i - 1)}\left(\sum_{i=1}^{N}\sum_{t=2}^{T_i} (\widehat{z_{it}z_{it}^T}) - \right. \quad (34)$$
$$\left. A^{(1)}\sum_{i=1}^{N}\sum_{t=2}^{T_i} (\widehat{z_{i(t-1)}z'_{it}}) - \sum_{i=1}^{N}\sum_{t=2}^{T_i} B^{(1)}\Delta_{i,t,t-1}\widehat{z_{it}}'\right)$$

Parameter R:

$$R^{(1)} = \frac{1}{\sum_{i=1}^{N} T_i}\sum_{i=1}^{N}\sum_{t=2}^{T_i} (y_{it}y'_{it} - C^{(1)}\widehat{z_{it}}y'_{it}) \quad (35)$$

It should be appreciated that the steps of "receiving", "providing", "using", "obtaining", "performing" and the like, as used herein, include the application of various mathematical operations applied to data and signals, according to any specific context or for any specific purpose. It should be appreciated that such steps may be facilitated or otherwise effectuated by a microprocessor executing machine readable program instructions retrieved from a memory or storage device.

Flow Diagram of One Embodiment

Figure 2:
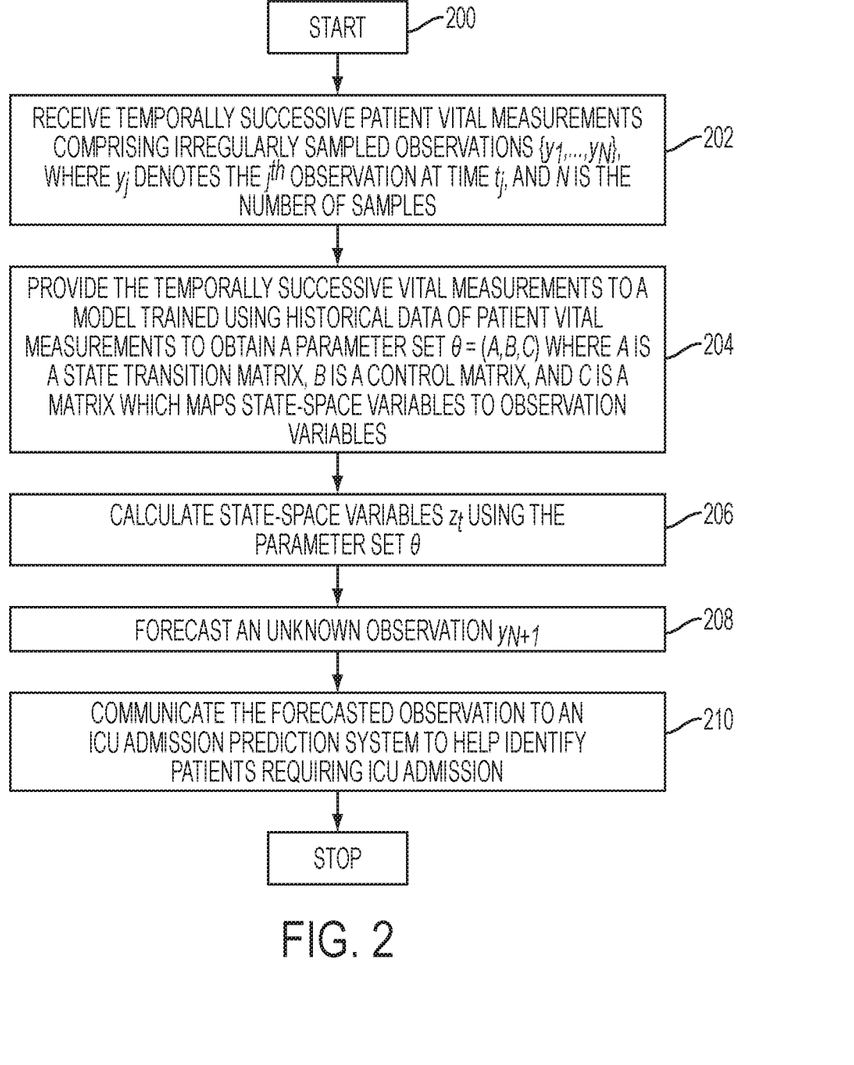
FIG. 2 is a flow diagram which illustrates one embodiment of the present method for obtaining an unknown patient vital measurement for healthcare analytics.

Reference is now being made to the flow diagram of FIG. 2 which illustrates one embodiment of the present method for obtaining an unknown patient vital measurement for healthcare analytics. Flow processing begins at step 200 and immediately proceeds to step 202.

At step 202, receive temporally successive patient vital measurements comprising irregularly sampled observations $\{y_1, \ldots, y_N\}$, where $y_j$ denotes the $j^{th}$ observation at time and N is the number of samples.

At step 204, provide the temporally successive vital measurements to a model trained using historical data of patient vital measurements to obtain a parameter set θ=(A, B, C) where A is a state transition matrix, B is a control matrix, and C is a matrix which maps state-space variables to observation variables.

At step 206, calculate state-space variables $z_t$ using the parameter set θ.

At step 208, forecast an unknown observation $y_{N+1}$. In another embodiment, and an unknown observation $y_t$ is imputed, where 1<t<N.

At step 210, communicate the forecasted observation to an ICU Admission Prediction System to help identify patients requiring ICU admission. In another embodiment, the forecasted observation is communicated to an Emerging Complications Prediction System to help identify patients at risk for developing complications during their hospital stay. In this embodiment, further processing stops.

It should be appreciated that the flow diagrams depicted herein are illustrative. One or more of the operations illustrated in the flow diagrams may be performed in a differing order. Other operations may be added, modified, enhanced, or consolidated. Variations thereof are intended to fall within the scope of the appended claims. Various steps of the flow diagram may be performed by one or more processors executing machine readable program instructions obtained from a memory.

Example Networked System

Figure 3:
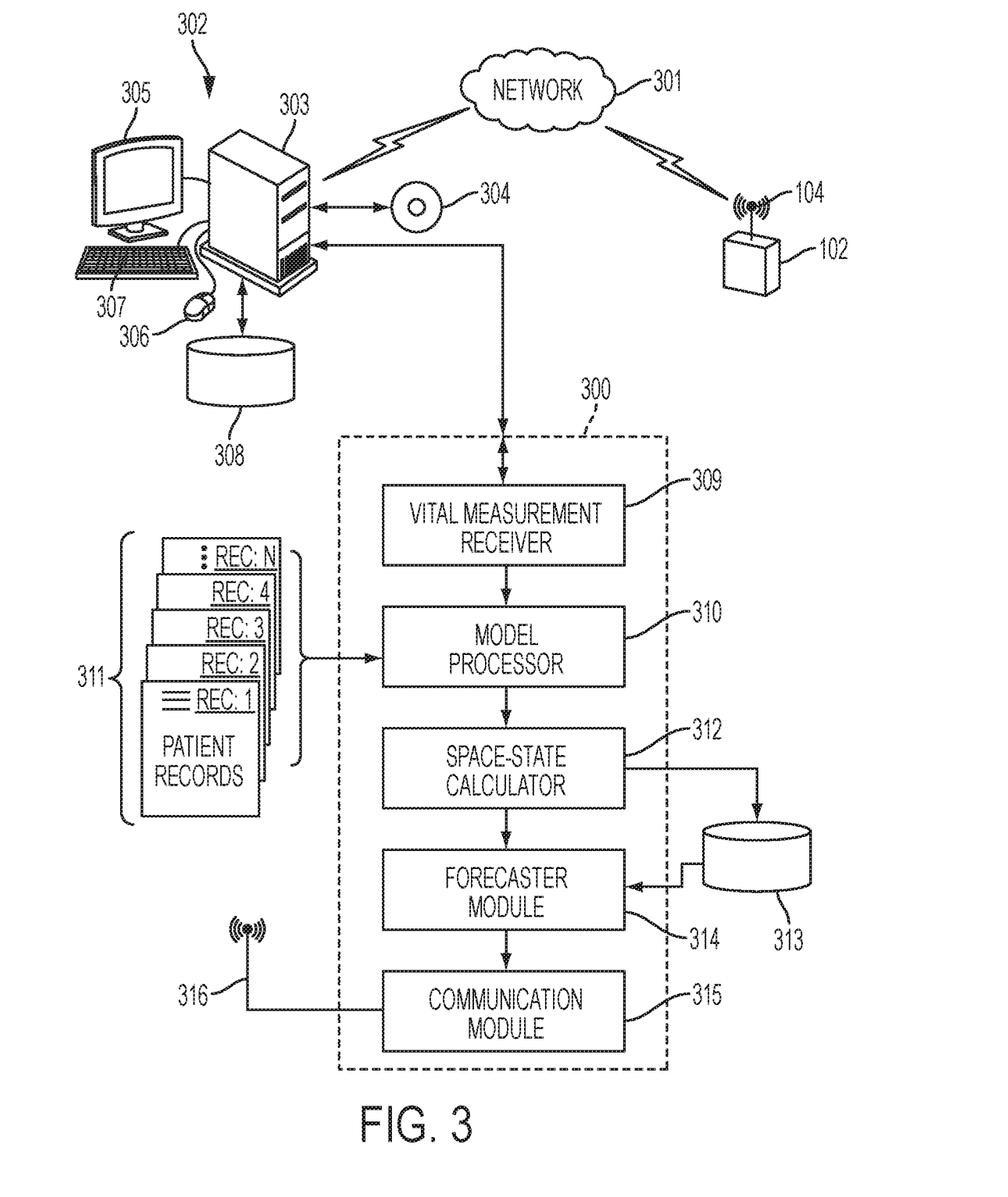
FIG. 3 shows a functional block diagram of an example networked system for implementing various aspects of the present method described with respect to the flow diagram of FIG. 2.

Reference is now being made to FIG. 3 which shows a functional block diagram of an example networked system for implementing various aspects of the present method described with respect to the flow diagram of FIG. 2. The system 300 illustrates a plurality of modules, processors, and components placed in networked communication with a workstation 302 wherein vital measurements transmitted over network 301 via transmissive element 104 by vital measurement device 102 are received for processing.

Workstation 302 includes a hard drive (internal to computer housing 303) which reads/writes to a computer readable media 304 such as a floppy disk, optical disk, CD-ROM, DVD, magnetic tape, etc. The computer case houses a motherboard with a processor and memory, a communications link such as a network card, graphics card, and the like, and other software and hardware to perform the functionality of a computing device as is generally known in the arts. The workstation includes a graphical user interface which, in various embodiments, comprises display 305 such as a CRT, LCD, touch screen, etc., a mouse 306 and keyboard 307. Information may be entered by a user of the present system using the graphical user interface. It should be appreciated that workstation has an operating system and other specialized software configured to display a wide variety of numeric values, text, scroll bars, pull-down menus with user selectable options, and the like, for entering, selecting, or modifying information displayed on the display device. The embodiment shown is only illustrative. Although shown as a desktop computer, it should be appreciated that computer 302 can be any of a laptop, mainframe, client/server, or a special purpose computer such as an ASIC, circuit board, dedicated processor, or the like. Any of the Information obtained from any of the modules of system 300 can be saved to database 308.

Vital Measurement Receiver 309 receives temporally successive patient vital measurements comprising irregularly sampled observations from the workstation. Model Processor 310 receives the temporally successive vital measurements and generates a parameter set θ=(A,B,C,Q,R). The Model Processor used the historical patient records (collectively at 311) to train the model. Space-State Calculator 312 receives the parameter set θ and proceeds to calculate state-space variables $z_t$. The results thereof are stored to storage device 313. Forecaster Module 314 retrieves the state-spaced variables from the storage device and proceeds to forecast an unknown observation $y_{N+1}$. In another embodiment, Module 314 imputes an unknown observation $y_t$ is imputed, where $1<t<N$. Communication Module 315 receives the forecasted observation(s) and/or the imputed observation(s) and proceeds to transmit those results via antenna 316 to an ICU Admission Prediction System over network 301 wherein the results are used to help identify patients requiring ICU admission. In another embodiment, the forecasted and/or imputed observation(s) are communicated to an Emerging Complications Prediction System to help identify patients at risk for developing complications during their hospital stay.

It should be understood that any of the modules and processing units of FIG. 3 are in communication with workstation 302 via pathways shown and not shown and may further be in communication with one or more remote devices over network 301. Any of the modules may communicate with storage devices 308 and 313 via pathways shown and not shown and may store/retrieve parameter values, functions, patient records, vital measurements, historical data, to name a few, and retrieve machine readable/executable program instructions required to perform their intended functions. Some or all of the functionality for any of the modules of the functional block diagram of FIG. 3 may be performed, in whole or in part, by components internal to workstation 302 or by a special purpose computer system.

Various modules may designate one or more components which may, in turn, comprise software and/or hardware designed to perform the intended function. A plurality of modules may collectively perform a single function. Each module may have a specialized processor and memory capable of executing machine readable program instructions. A module may comprise a single piece of hardware such as an ASIC, electronic circuit, or special purpose processor. A plurality of modules may be executed by either a single special purpose computer system or a plurality of special purpose systems operating in parallel. Connections between modules include both physical and logical connections. Modules may further include one or more software/hardware components which may further comprise an operating system, drivers, device controllers, and other devices some or all of which may be connected via network 301. It is also contemplated that one or more aspects of the present method may be implemented on a dedicated computer system and may also be practiced in distributed computing environments where tasks are performed by remote devices that are linked through a network.

Performance Results

Figure 4:
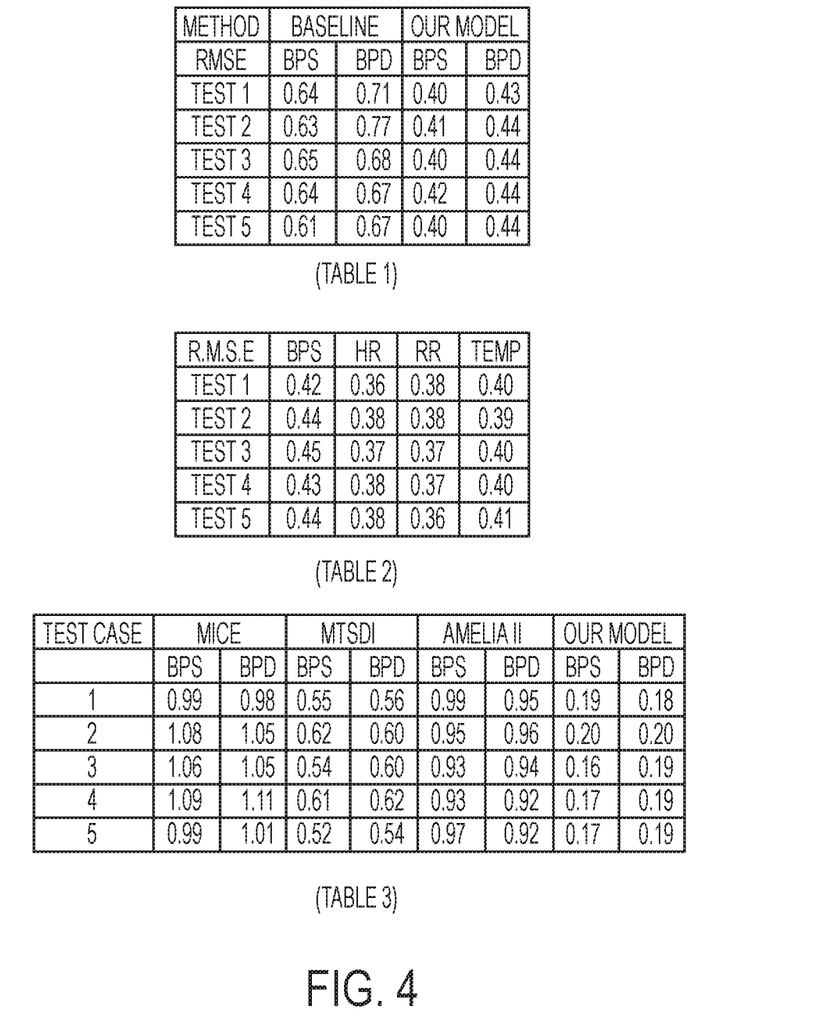
FIG. 4 shows TABLES 1, 2 and 3 containing various performance results of the methods disclosed herein.

Historical data of patients admitted in hospitals in the USA was obtained (from the Midas+ Non-PHI Analytics Warehouse). The vital measurements were Systolic BP (BPS), Diastolic BP (BPD), Respiration Rate (RR), Heart Rate (HR), and Temperature (TEMP). The efficacy of our model was test for blood pressure. The (systolic and diastolic) blood pressure of 500 patients during their stay at hospital were used to train the model in order to make 1-step-ahead forecasts. For comparison, we also learn the parameters in a traditional Kalman Filter setting where the parameters are learned using a single long-observation sequence. This model was our Baseline. Here, a sequence with X number of BP readings was utilized. Once, the parameters θ were learned, both the filters are applied to 5 different test sets each containing 200 distinct records. For evaluation purposes, the Root Mean Squared Error (RMSE) of the forecasts were computed by:

$$\sqrt{\frac{\sum_{i=1}^{N}(\hat{y}_i - y_i)^2}{n}}$$

where $\hat{s}_t$ is the forecast given for the true value $y_i$ and n is the total number of forecasts made. In FIG. 4, TABLE 1 shows results where the dimension of the observations, p=2 and the dimension of the hidden states, k=2. TABLE 2 shows results where p=4 and k=4. As can be seen, our model produced better forecasts than a more traditional data forecasting approaches with RMSE's that are much lower. To test our model's ability to impute an unknown observation, we randomly removed 20% of the values from both systolic and diastolic blood pressures, imputed data using our model, and checked the accuracy of the imputed observation against the same test sets used previously. We compared our imputed results to well-known imputation techniques: MICE, MTSDI, and AMELIA-II, as are widely understood. The RMSE's for each are given in TABLE 3. As shown, our model has the least RMSE thus demonstration the efficacy of our imputation method when compared to prior art techniques.

Various Embodiments

Various aspects of the systems and methods described herein are intended to be incorporated in an article of manufacture which may be shipped, sold, leased, or otherwise provided separately either alone or as part of a product suite. The above-disclosed features and functions or alternatives thereof, may be combined into other systems and applications. Presently unforeseen or unanticipated alternatives, modifications, variations, or improvements may become apparent and/or subsequently made by those skilled in the art and, further, may be desirably combined into other different systems or applications. Changes to the above-described embodiments may be made without departing from the spirit and scope of the invention. The teachings of any printed publications including patents and patent applications, are each separately hereby incorporated by reference in their entirety.

What is claimed is:

1. A computer implemented method for obtaining an unknown patient vital measurement for healthcare analytics, the method comprising:

receiving, by a processor, temporally successive patient vital measurements comprising irregularly sampled observations $\{y_1, \ldots, y_N\}$, where $y_j$ denotes the $j^{th}$ observation at time $t_j$, and N is the number of samples;

communicating, by a processor, the temporally successive vital measurements to a model trained using historical data of patient vital measurements, the model generating a parameter set θ=(A,B,C,Q,R), where A is a state transition matrix, B is a control matrix, C is a matrix which maps state-space variables to observation variables, Q is an amount of noise in the state-space variables, and R is an amount of noise in the observation variables;

calculating, by a processor, state-space variables $z_t$ using the parameter set θ generated by the model; and performing, by a processor, one of: forecasting an unknown observation $y_{N+1}$, and imputing an unknown observation $y_t$, where $1<t<N$.

2. The computer implemented method of claim 1, wherein the patient vital measurements are obtained from Electronic Medical Records.

3. The computer implemented method of claim 1, wherein the vital measurements are any of: blood pressure, respiration rate, heart rate, body temperature, blood glucose, oxygen saturation, blood $CO_2$, Glasgow Coma Scale, and a combination hereof.

4. The computer implemented method of claim 1, wherein $z_t$ comprises:

$$z_t = Az_{t-1} + B\Delta_{t,t-1} + \epsilon_t$$

where $\Delta_{t,t-1}$ denotes a time difference between the $t^{th}$ and the $(t-1)^{th}$ observation, $\epsilon_t \sim \mathcal{N}(0, Q)$ is approximated by a zero-mean Gaussian with an unknown co-variance, and Q is an amount of noise in the state-space variables.

5. The computer implemented method of claim 1, wherein $y_t$ comprises:

$$y_t = Cz_t + \delta_t$$

where $\delta_t \sim \mathcal{N}(0, R)$ is approximated by a zero-mean Gaussian with an unknown co-variance and R is an amount of noise in the observation variables.

6. The computer implemented method of claim 1, further comprising communicating the obtained observation to an ICU Admission Prediction System to help identify patients requiring ICU admission.

7. The computer implemented method of claim 1, further comprising communicating the obtained observation to an Emerging Complications Prediction System to help identify patients at risk for developing complications during their hospital stay.

8. The computer implemented method of claim 1, further comprising updating the historical data of patient vital measurements with the forecasted observation $y_{N+1}$.

9. The computer implemented method of claim 1, further comprising updating the historical data of patient vital measurements with the imputed observation $y_t$.

10. A system for obtaining an unknown patient vital measurement for healthcare analytics, the system comprising:
   a storage device; and
   a processor in communication with the storage device, the processor executing machine readable instructions for performing:
      receiving temporally successive patient vital measurements comprising irregularly sampled observations $\{y_1, \ldots, y_N\}$, where $y_j$ denotes the $j^{th}$ observation at time $t_j$, and N is the number of samples;
      communicating the temporally successive vital measurements to a model trained using historical data of patient vital measurements, the model generating a parameter set $\theta = (A,B,C,Q,R)$, where A is a state transition matrix, B is a control matrix, C is a matrix which maps state-space variables to observation variables, Q is an amount of noise in the state-space variables, and R is an amount of noise in the observation variables;
      calculating state-space variables $z_t$ using the parameter set $\theta$ generated by the model;
      performing one of: forecasting an unknown observation $y_{N+1}$, and imputing an unknown observation $y_t$, where $1 < t < N$; and
      storing the obtained observation to the storage device.

11. The system of claim 10, wherein the patient vital measurements are obtained from Electronic Medical Records.

12. The system of claim 10, wherein $z_t$ comprises:

$$z_t = Az_{t-1} + B\Delta_{t,t-1} + \epsilon_t$$

where $\Delta_{t,t-1}$ denotes a time difference between the $t^{th}$ and the $(t-1)^{th}$ observation, $\epsilon_t \sim \mathcal{N}(0, Q)$ is approximated by a zero-mean Gaussian with an unknown co-variance, and Q is an amount of noise in the state-space variables.

13. The system of claim 10, wherein $y_t$ comprises:

$$y_t = Cz_t + \delta_t$$

where $\delta_t \sim \mathcal{N}(0, R)$ is approximated by a zero-mean Gaussian with an unknown co-variance and R is an amount of noise in the observation variables.

14. The system of claim 10, further comprising communicating the obtained observation to an ICU Admission Prediction System to help identify patients requiring ICU admission.

15. The system of claim 10, further comprising communicating the obtained observation to an Emerging Complications Prediction System to help identify patients at risk for developing complications during their hospital stay.

16. The system of claim 10, further comprising updating the historical data of patient vital measurements with the forecasted observation $y_{N+1}$.

17. The system of claim 9, further comprising updating the historical data of patient vital measurements with the imputed observation $y_t$.

18. The system of claim 10, wherein the vital measurements are any of: blood pressure, respiration rate, heart rate, body temperature, blood glucose, oxygen saturation, blood $CO_2$, Glasgow Coma Scale, and a combination hereof.

* * * * *